United States Patent
Guethe et al.

(10) Patent No.: US 10,557,378 B2
(45) Date of Patent: Feb. 11, 2020

(54) SYSTEM AND METHOD FOR REGULATING CONDENSATION OF FLUE GAS IN A STEAM GENERATOR

(71) Applicant: GENERAL ELECTRIC TECHNOLOGY GMBH, Baden (CH)

(72) Inventors: Felix Guethe, Basel (CH); John Martin Nilsson, Wettingen (CH); Stefano Bernero, Oberrohrdorf (CH); Mariah Couzzi Carneiro, Huttikon (CH)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 601 days.

(21) Appl. No.: 15/062,806

(22) Filed: Mar. 7, 2016

(65) Prior Publication Data

US 2017/0254227 A1 Sep. 7, 2017

(51) Int. Cl.
*F01K 23/10* (2006.01)
*G01N 21/65* (2006.01)
(Continued)

(52) U.S. Cl.
CPC .......... *F01K 23/101* (2013.01); *F22B 37/025* (2013.01); *F23J 15/00* (2013.01);
(Continued)

(58) Field of Classification Search
CPC .......... F01K 23/101; F23J 15/00; F23J 15/08; G01N 2021/399; G01N 21/3504; G01N 21/65; Y02E 20/16; F22B 37/025
See application file for complete search history.

(56) References Cited

U.S. PATENT DOCUMENTS

| 4,245,573 A | 1/1981 | Dixit et al. | |
| 4,444,128 A * | 4/1984 | Monro | F23J 15/006 110/215 |
| 4,542,621 A * | 9/1985 | Andersson | F02C 3/205 423/242.1 |

(Continued)

FOREIGN PATENT DOCUMENTS

| EP | 0 618 404 A1 | 10/1994 |
| WO | 2005079324 A2 | 9/2005 |

OTHER PUBLICATIONS

Peggy Skotnicki, Identification and Determination of Sulfur Trioxide in Sulfur Dioxide by Raman Spectrometry, Nov. 1973.*
(Continued)

*Primary Examiner* — Jesse S Bogue
(74) *Attorney, Agent, or Firm* — Grogan, Tuccillo & Vanderleeden, LLP

(57) ABSTRACT

A system for regulating condensation of a flue gas in a steam generator is provided. The system includes a temperature controller and a flue gas analyzer. The temperature controller is configured to control a temperature of a component of the steam generator, the component being in heating-contact with the flue gas. The flue gas analyzer is configured to communicate with the temperature controller and to obtain a measurement of an amount of an acid-forming compound in the flue gas. The temperature controller adjusts the temperature of the component based at least in part on the measurement such that the temperature of the component is above an acid dew point of the flue gas when the component is in heating-contact with the flue gas.

20 Claims, 6 Drawing Sheets

(51) Int. Cl.
*F22B 37/02* (2006.01)
*F23J 15/00* (2006.01)
*F23J 15/08* (2006.01)
G01N 21/3504 (2014.01)
G01N 21/39 (2006.01)

(52) U.S. Cl.
CPC .............. *F23J 15/08* (2013.01); *G01N 21/65* (2013.01); *G01N 21/3504* (2013.01); *G01N 2021/399* (2013.01); *Y02E 20/16* (2013.01)

(56) References Cited

U.S. PATENT DOCUMENTS

| | | | |
|---|---|---|---|
| 4,976,100 A | 12/1990 | Lee | |
| 5,044,424 A * | 9/1991 | Monro | B01D 53/504 165/10 |
| 7,618,602 B2 | 11/2009 | Meserole et al. | |
| 8,107,080 B2 * | 1/2012 | Socha | B01D 46/4263 356/436 |
| 8,368,896 B1 * | 2/2013 | Li | F23N 5/082 250/339.08 |
| 8,778,041 B2 * | 7/2014 | Mitsui | B01D 53/343 55/282.3 |
| 2001/0007190 A1 * | 7/2001 | Schmid | F01K 23/106 60/39.182 |
| 2003/0184320 A1 | 10/2003 | Breen et al. | |
| 2004/0187688 A1 * | 9/2004 | Liebig | B01D 19/0047 95/251 |
| 2010/0037678 A1 * | 2/2010 | Chothani | G01N 27/14 73/25.01 |
| 2011/0045422 A1 * | 2/2011 | Tanca | F23D 1/02 431/76 |
| 2018/0059013 A1 * | 3/2018 | Brechtel | G01N 33/0042 |

OTHER PUBLICATIONS

Extended European Search Report and Opinion issued in connection with corresponding EP Application No. 17158893.2 dated Jul. 20, 2017.

* cited by examiner

SYSTEM AND METHOD FOR REGULATING CONDENSATION OF FLUE GAS IN A STEAM GENERATOR

BACKGROUND

Technical Field

Embodiments of the invention relate generally to power generation and, more specifically, to a system and method for regulating condensation of flue gas in a steam generator.

Discussion of Art

Many electrical power generation plants utilize steam generators to power turbines, which generate electrical power. Such plants typically use boilers and/or heat recovery steam generators ("HRSGs") to generate steam. Boilers generate steam by heating water via combusting a fuel, which in turn produces flue gas. HRSGs generate steam by heating water via thermal energy recovered from flue gas. Both boilers and HRGSs heat the water used to generate steam by containing it in a conduit that is exposed to a flue gas.

The efficiency of a steam generator may be partially determined by the "approach point," which, as used herein, refers to the difference between the temperature of the generated steam as it leaves the steam generator and the temperature of the water as it enters the steam generator. The larger the approach point, the more thermal energy the generated steam can absorb/store from a flue gas, and the greater the efficiency of the steam generator. Accordingly, some steam generators increase the approach point by allowing water to enter the conduit at low temperatures.

In such steam generators, however, the flue gas may include acid-forming compounds that will condense out of the gas at or below a certain temperature, hereinafter also referred to as the "acid dew point" of the flue gas. The value of the acid dew point, i.e., the temperature corresponding to the condensation of acid-forming compounds, is partially determined by the amount/concentration of acid-forming compounds in the flue gas. For example, the higher the amount/concentration of acid-forming compounds in the flue gas, the lower the temperature corresponding to the acid dew point.

Accordingly, if the temperature of the water entering the conduit is sufficiently low, the water may cool the conduit to a point below the acid dew point of the flue gas, thus allowing the acid-forming compounds to condense out of the flue gas and form acids. The formation of acids can potentially cause corrosion to the components of the steam generator—including the conduit.

As such, many steam generators are configured to keep the water entering the conduit at a temperature, hereinafter referred to as a "set temperature," that is high enough to prevent the conduit from being cooled to or below the acid dew point. The difference between the set temperature and the acid dew point is known as a "margin of safety." Many steam generators, however, are unable to accurately measure the amount/concentration of the acid-forming compounds in the flue gas. As such, many steam generators are unable to accurately determine the acid dew point. Moreover, the amount/concentration of the acid-forming compounds in the flue gas may fluctuate over time. As a result, many steam generators maintain a large/conservative margin of safety, which reduces the efficiency of the steam generator.

What is needed, therefore, is a system and method for regulating condensation of a flue gas in a steam generator to increase efficiency.

BRIEF DESCRIPTION

In an embodiment, a system for regulating condensation of a flue gas in a steam generator is provided. The system includes a temperature controller and a flue gas analyzer. The temperature controller is configured to control a temperature of a component of the steam generator, the component being in heating-contact with the flue gas. The flue gas analyzer is configured to communicate with the temperature controller and to obtain a measurement of an amount of an acid-forming compound in the flue gas. The temperature controller adjusts the temperature of the component based at least in part on the measurement such that the temperature of the component is above an acid dew point of the flue gas when the component is in heating-contact with the flue gas.

In another embodiment, a method for regulating condensation of a flue gas in a steam generator is provided. The method includes obtaining a measurement of an amount of an acid-forming compound in the flue gas via a flue gas analyzer, the flue gas being in heating-contact with one or more components of the steam generator. The method further includes controlling a temperature of the one or more components via a temperature controller in communication with the flue gas analyzer and based at least in part on the measurement such that the temperature of the one or more components is above an acid dew point of the flue gas.

In yet another embodiment, a combined cycle power generation plant that regulates condensation of a flue gas is provided. The combined cycle power generation plant includes a primary generator, a heat recovery steam generator, one or more components, a temperature controller, and a flue gas analyzer. The primary generator generates the flue gas by combusting a fuel. The heat recovery steam generator is fluidly connected to the primary generator such that the flue gas flows from the primary generator to the heat recovery steam generator. The one or more components are disposed in at least one of the primary generator and the heat recovery steam generator, and are configured to be in heating-contact with the flue gas. The temperature controller is configured to control a temperature of the one or more components. The flue gas analyzer is in communication with the temperature controller and is configured to obtain a measurement of an acid-forming compound in the flue gas. The temperature controller adjusts the temperature of the one or more components based at least in part on the measurement such that the temperature of the one or more components is above an acid dew point of the flue gas when the one or more components are in heating-contact with the flue gas.

DRAWINGS

The present invention will be better understood from reading the following description of non-limiting embodiments, with reference to the attached drawings, wherein below:

DETAILED DESCRIPTION

Figure 1:
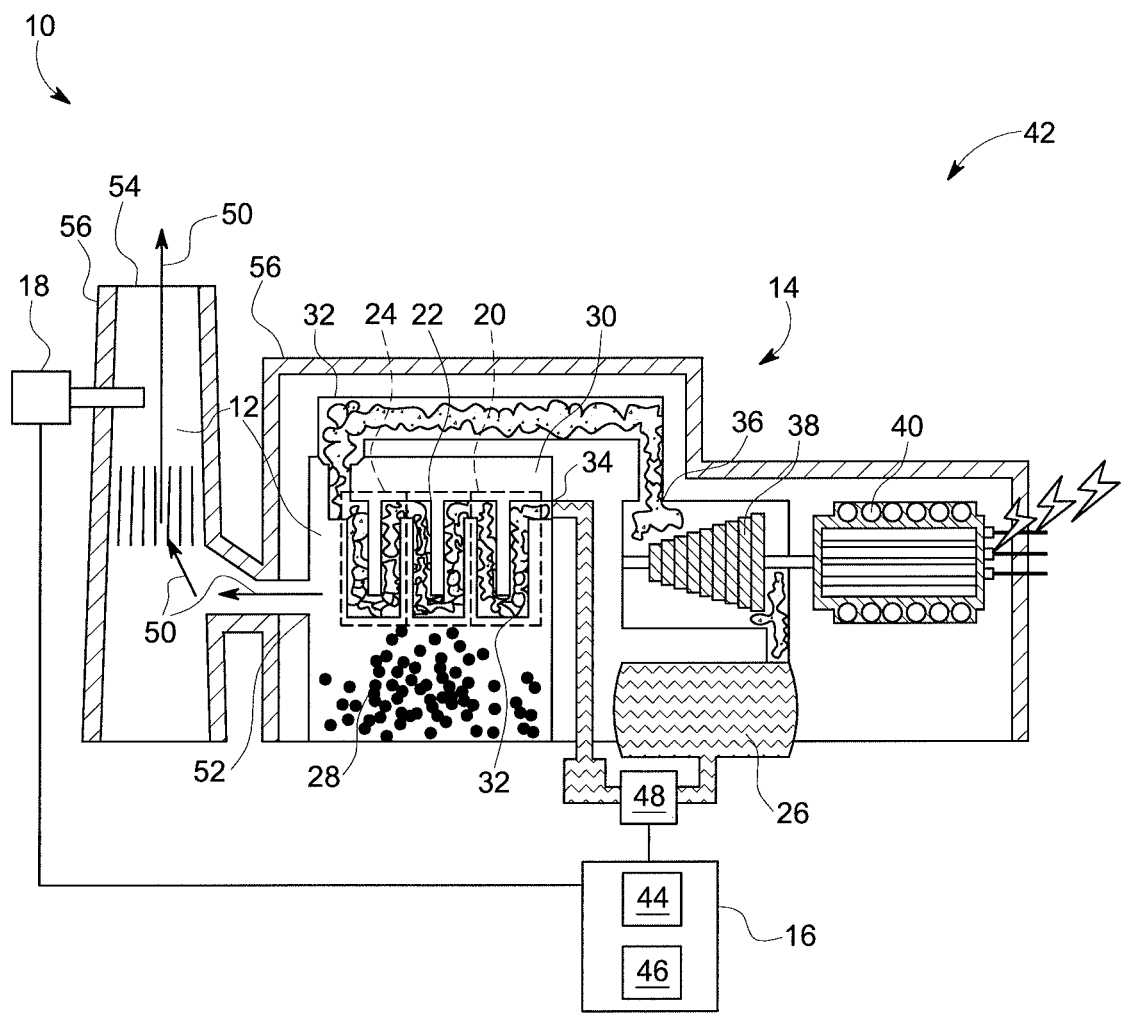
FIG. 1 is a diagram of a system for regulating condensation of a flue gas in a steam generator in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. As also used herein, the term "fluidly connected" means that the referenced elements are connected such that a fluid (to include a liquid, gas, and/or plasma) may flow from one to the other. Accordingly, the terms "upstream" and "down stream," as used herein, describe the position of the referenced elements with respect to a flow path of a fluid flowing between and/or near the referenced elements.

Additionally, as used herein, the term "fill" includes both fully and partially filling a containing object with a filling object. As also used herein, the term "heating-contact" means that the referenced objects are in proximity of one another such that heat/thermal energy can transfer between them. As further used herein, the term "acid-forming compound" refers to chemical compounds that are capable of reacting to form acids. As also used herein, the term "corrosive" means capable of causing damage to a material. Additionally, the term "real time" means a level of processing responsiveness that a user senses as sufficiently immediate or that enables the processor to keep up with an external process.

Further, while the embodiments disclosed herein are described with respect to steam generators, it is to be understood that embodiments of the present invention are equally applicable to any device and/or process in which the condensation of a flue gas requires regulation in order to prevent and/or reduce the formation of acids.

Accordingly, referring to FIG. 1, a system 10 for regulating condensation of a flue gas 12 in a steam generator 14 includes a temperature controller 16 and a flue gas analyzer 18. The temperature controller 16 is configured to control a temperature of one or more components 20, 22, and 24, of the steam generator 14, which are configured to be in heating-contact with the flue gas 12. The flue gas analyzer 18 is configured to electrically communicate with the temperature controller 16 and to obtain a measurement of an amount of an acid-forming compound in the flue gas 12. The temperature controller 16 is further configured to adjust the temperature of the one or more components 20, 22, and 24 such that the temperature of the one or more components 20, 22, and 24 is above an acid dew point of the flue gas 12 when the one or more components 20, 22, and 24 are in heating-contact with the flue gas 12.

As shown in FIG. 1, the steam generator 14 may be a boiler that generates steam by heating a working-medium 26, via combusting a fuel 28 in a combustion chamber 30, which produces the flue gas 12. As used herein, the term "working-medium" means water and/or any other medium capable of storing thermal energy. Accordingly, in embodiments, the working-medium 26 heated by the boiler 14 to generate steam may be contained in a conduit 32 formed by the one or more components 20, 22, and 24. For example, in such embodiments, the conduit 32 may be formed by an economizer 20, evaporator 22, and/or superheater 24. The conduit 32 may include a first opening 34, a second opening 36, and may be configured to be in heating-contact with the flue gas 12 such that the working-medium 26 is heated/converted into steam as it flows into the first opening 34, through the conduit 32, and out the second opening 36. The resulting steam may then be used to power a turbine 38 that in turn powers an electrical generator 40 of a power plant 42. As is to be understood, while FIG. 1, depicts the steam generator 14 as a boiler, in embodiments, the steam generator 14 may be a HRSG (shown as 114 in FIG. 6).

The temperature controller 16 may include at least one processor 44 and a memory device 46 that stores an application. As can be seen, in FIG. 1, in embodiments, the temperature controller 16 may be in electronic communication with the flue gas analyzer 18 such that the temperature controller 16 controls the temperature of the components 20, 22, and 24 based at least in part on the measurement of the amount of the acid-forming compound in the flue gas 12. In other words, the temperature controller 16 may calculate the acid dew point based on the measurement obtained by the flue gas analyzer 18, and then adjust the temperature of the components 20, 22, and 24 such that it remains above the acid dew point.

As illustrated in FIG. 1, the temperature controller 16 may be configured to control a heating device 48, such as a heating coil and/or other device for applying heat to the components 20, 22, and 24. In embodiments, the heating device 48 may be configured to control the temperature of the components 20, 22, and 24 by controlling a temperature of the working-medium 26 as it enters the first opening 34 of the conduit 32. The temperature controller 16 may be further configured to keep the temperature of the components 20, 22, and 24 at or near a set temperature. In embodiments, the set temperature may be based at least in part on a desired margin of safety and the acid dew point. Accordingly, the temperature controller 16 may calculate the set temperature such that the set temperature is higher than the acid dew point by an amount greater than or equal to the desired margin of safety. As is to be understood, the temperature controller 16 may be in electronic communication with one or more temperature sensors that sense the temperature of the working-medium 26 and/or the components 20, 22, and 24.

Additionally, in embodiments, the temperature controller 16 may calculate the set temperature at real time or near real time such that the temperature of the working-medium 26 fluctuates as the acid dew point fluctuates. In other words, the system 10 allows the approach point to shrink and expand as the acid dew point rises and falls, respectively. Thus, as is to be appreciated, since the approach point can be adjusted in real time or near real time, the margin of safety may be reduced.

As further shown in FIG. 1, the flue gas analyzer 18 may be disposed in a flow path 50 of the flue gas 12. The flow path 50 may include a first opening 52, a second opening 54, and may be configured to direct the flue gas 12. In embodiments, the first opening 52 is fluidly connected to the combustion chamber 30 such that the flue gas 12 may flow from the combustion chamber 30, along the flow path 50, and out of the second opening 54. In embodiments, the flow path 50 may be defined by a housing 56 of the steam generator 14.

The fuel 28 combusted in the combustion chamber 30 may be a coal, an oil, and/or a gas. As is to be appreciated, combustion of the fuel 30 may result in the formation and/or release of acid-forming compounds, which form part of the flue gas 12. In embodiments, the acid-forming compounds may include: sulfur dioxide ("SO2"); sulfur trioxide ("SO3"); sulfuric acid ("H2SO4"); other sulfur based compounds (SOx); and/or other acid-forming compounds. As is to be further appreciated, the flue gas 12 cools as it flows through the flow path 50, which in turn causes the mole fractions of the acid-forming compounds in the flue gas 12 to vary from one section of the flow path 50 to another.

Figure 2:
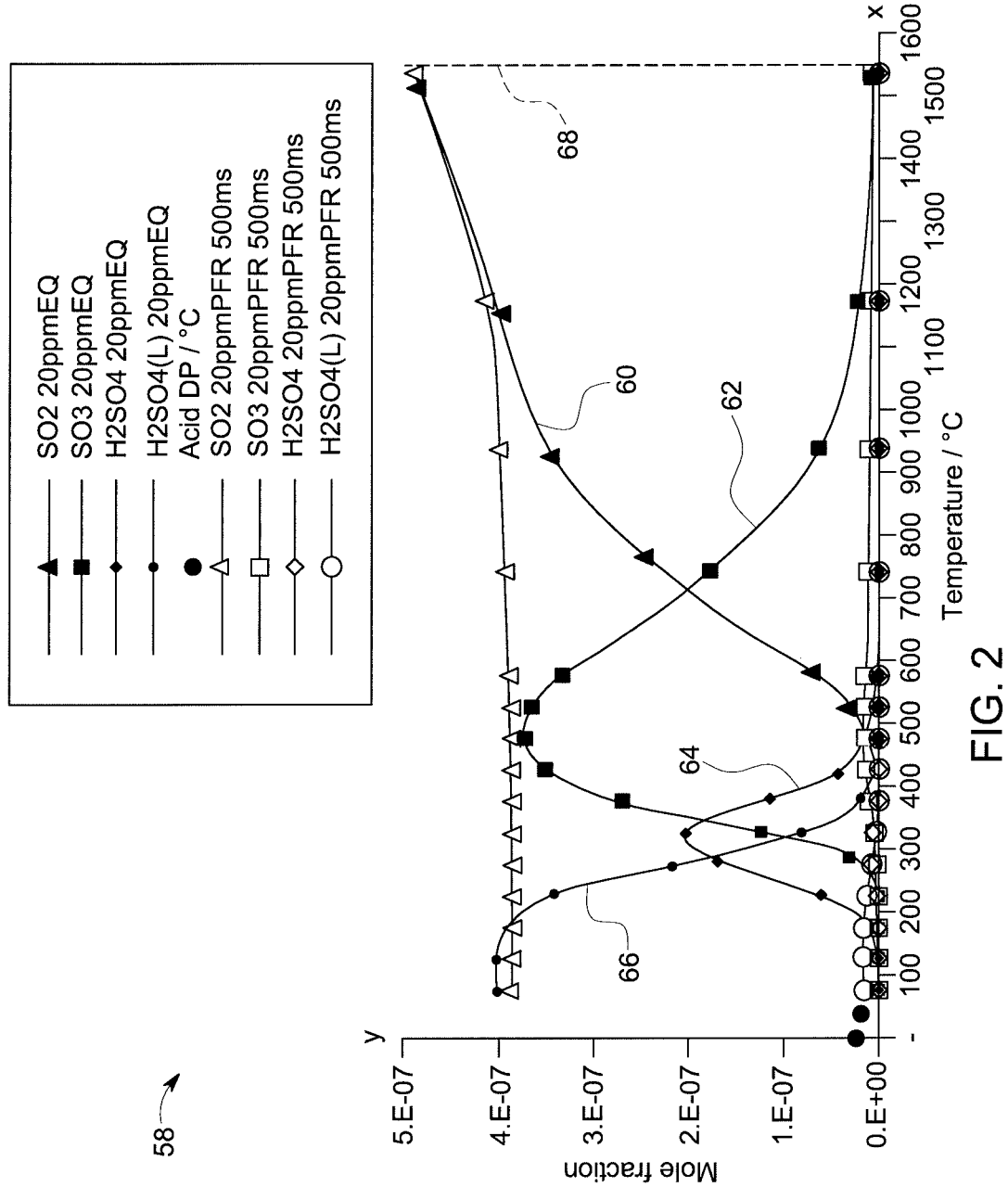
FIG. 2 is a graph that depicts the mole fractions of various acid-forming compounds present in the flue gas across a range of temperatures in accordance with an embodiment of the invention.
Figure 3:
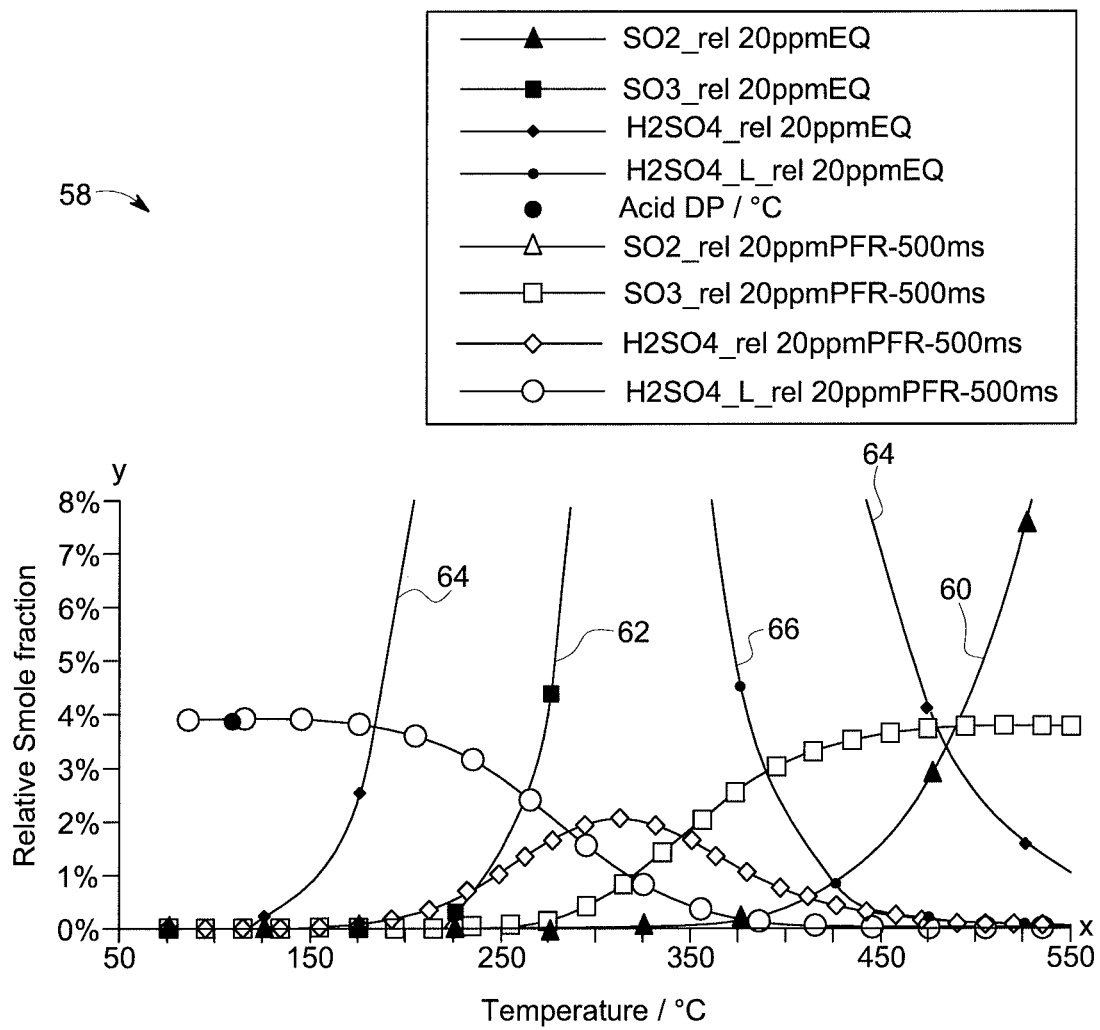
FIG. 3 is an enlarged view of the graph of FIG. 2.

For example, turning now to FIGS. 2 and 3, a graph 58 that depicts the mole fractions (y-axis/domain) of various acid-forming compounds that may be present in the flue gas 12 across a range of temperatures (x-axis/range) in accordance with an embodiment of the invention is shown. As shown in FIGS. 2 and 3, lines 60-66 represent SO2, SO3, H2SO4 (gas), and H2SO4 (liquid), respectively. As will be appreciated, while graph 58 depicts the acid-forming compounds as including SO2, SO3, H2SO4, it is to be understood that other compounds may be included in the flue gas 12.

As illustrated in FIGS. 2 and 3, when the flue gas 12 is first produced in the combustion chamber 30, represented by dashed line 68, the flue gas 12 may have an initial temperature between 1,500° C. and 1,600° C. As shown in FIG. 2, at such a temperature, SO2 60 forms the majority of the acid-forming compounds. As the temperature of the flue gas 12 decreases, the level of SO2 60 begins to decrease while the level of SO3 62 increases. At around 500° C., the amount of SO3 62 approximately equals the total amount of the acid-forming compounds in the flue gas 12. As the flue gas 12 continues to cool, the level of SO3 62 starts to decrease while the levels of H2SO4 (gas) 64 and H2SO4 (liquid) 66 increases. As the temperature of the flue gas 12 nears 200° C., nearly all the acid-forming compounds may condense out as H2SO4 (liquid) 66.

As stated above, the acid due point of the flue gas 12 is partially determined by the amount of the acid-forming compounds present in the flue gas 12. As can be seen by FIG. 2, the level of SO3 62 in the flue gas 12 may provide an indication of the total amount of the acid-forming compounds in the flue gas 12. As such, in embodiments, the flue gas analyzer 18 may be configured to measure the amount of SO3 62 in the flue gas 12. For example, as also shown in FIG. 2, the level of SO3 62 in the flue gas 12 at a temperature between 400° C. and 800° C. may accurately indicate the total amount of the acid-forming compounds in the flue gas 12. Accordingly, in embodiments, the flue gas analyzer 18 may be configured to obtain a measurement of the amount of the SO3 62 when the flue gas 12 has a temperature between 400° C. and 800° C. Further still, the level of SO3 62 in the flue gas 12 at a temperature at or near 500° C. may yet more accurately indicate the total amount of the acid-forming compounds in the flue gas 12. Accordingly, in embodiments, the flue gas analyzer 18 may be configured to obtain a measurement of the amount of the SO3 62 when the flue gas 12 has a temperature at or near 500° C.

Figure 4:
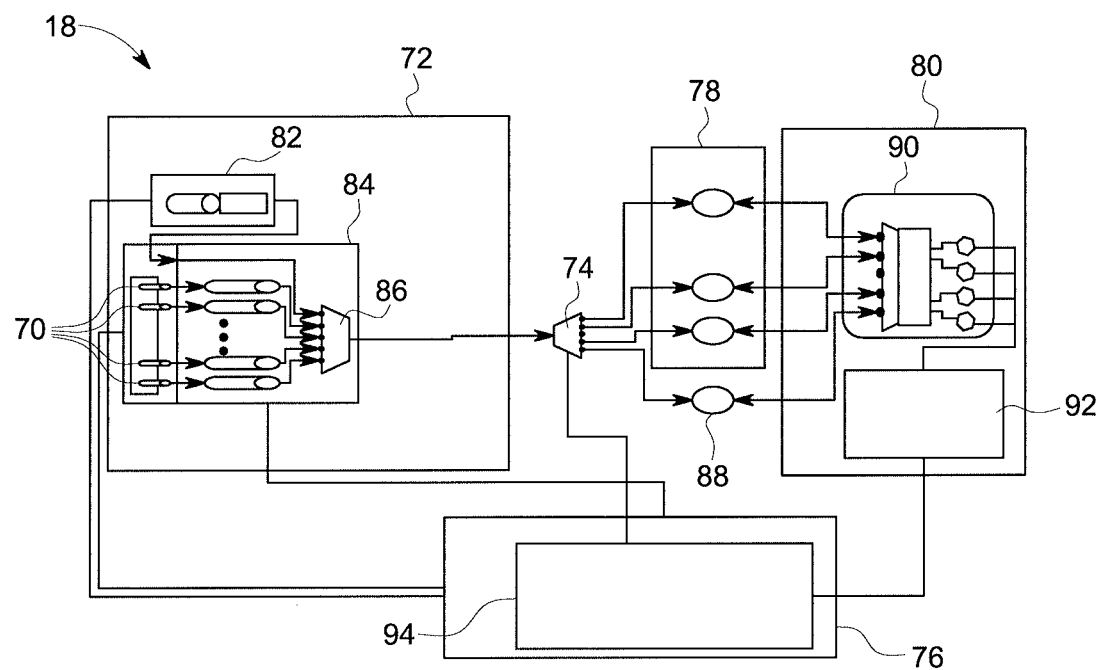
FIG. 4 is a diagram of a flue gas analyzer of the system of FIG. 1 in accordance with an embodiment of the invention.

Turning now to FIG. 4, the flue gas analyzer 18 may obtain the measurement of the acid-forming compound via a Raman process. For example, in embodiments, the flue gas analyzer 18 may be a spectroscopic sensor configured to detect/measure a v1 band around 1366 cm$^{-1}$. Additionally, in embodiments, the Raman process may be, but not limited to, a simulated Raman process, a surface-enhanced Raman process, a resonance Raman process, a tip-enhanced Raman process, a polarized Raman process, a transmission Raman process, a spatially offset Raman process, a hyper Raman process, and/or other similar spectroscopy based processes. As such, the flue gas analyzer 18 may include two or more lasers diodes 70. The flue gas analyzer 18 may further include a laser generator subsystem 72, a selector 74, a control sub system 76, detection windows 78, and a receiver 80.

The laser generator subsystem 72 may include a tunable pump 82, a laser array 84 that may include the two or more lasers diodes 70, and a combiner 86. The two or more lasers diodes 70 each generate individual beams, which are then combined by the combiner 86 into a combined beam. The combined beam is directed by the selector 74 through one or more of the detection windows 78, and/or a reference window 88, and then received by the receiver 80 via an optic bench 90. The receiver 80 may include an analogue manipulation and ADC module 92. The controller subsystem 76 may include a timing generator data acquisition module 94 and may be in electronic communication with, and direct the operation of, the laser generator subsystem 72, selector 74, detection windows 78, and/or the receiver 80.

While the flue gas analyzer 18 may obtain the measurement of the acid-forming compound via a Raman process, it is to be understood that other spectroscopic processes, such as infrared radiation ("IR") absorption, may be utilized as well. In such embodiments, the sensor may detect the v3 band, or other bands, of the SO3 molecules. For example, in such embodiments, the flue gas analyzer 18 may obtain the measurement of the acid-forming compound by IR absorption via a quantum cascade laser ("QCL") and/or a tunable diode laser ("TDL"). It is also to be appreciated, that in some embodiments, different transitions may be used to detect SO3 in the IR spectrum as well.

Figure 5:
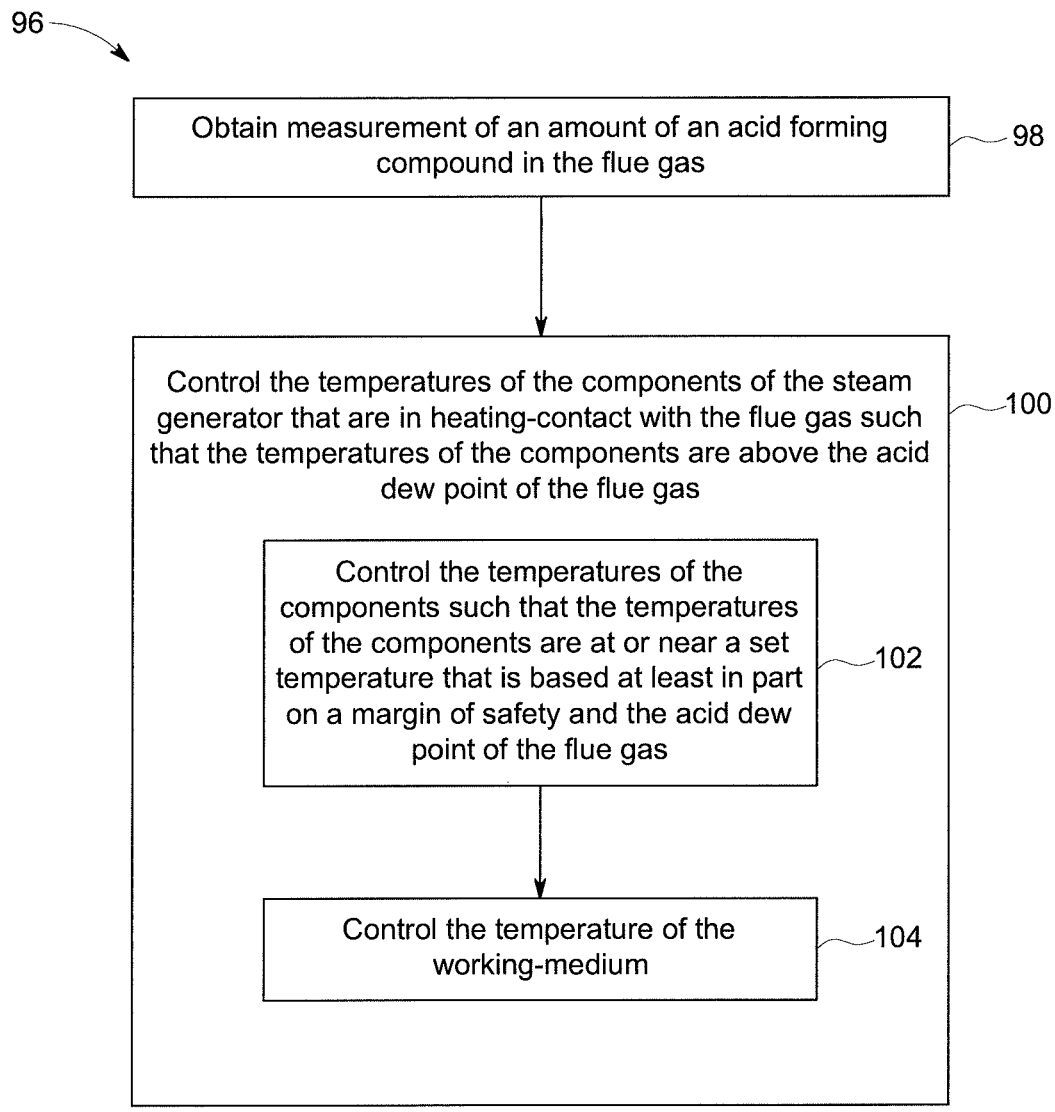
FIG. 5 is a flow chart depicting a method regulating condensation of a flue gas in a steam generator in accordance with an embodiment of the invention.

Turning now to FIG. 5, a method 96 for regulating condensation of a flue gas 12 in a steam generator 14 in accordance with an embodiment of the invention is shown. As will be appreciated, in embodiments, the application stored in the memory device 46 may be loaded into the at least one processor/CPU 44 such that the temperature controller 16 is adapted by the application to perform all, or part, of method 96. As can be seen in FIG. 5, the method includes obtaining 98, via the flue gas analyzer 18, a measurement of an amount of an acid-forming compound in the flue gas 12. As shown above, in embodiments, the flue gas 12 may be in heating-contact with the one or more components 20, 22, and 24 of the steam generator 14. The method 96 may further include controlling 100, via the temperature controller 16, the temperature of the one or more components 20, 22, and 24 such that the temperature of the one or more components 20, 22, and 24 is above an acid dew point of the flue gas 12.

In embodiments, controlling 100 the temperature of the one or more components 20, 22, and 24 such that the temperature of the one or more components 20, 22, and 24 is above an acid dew point of the flue gas 12 may include controlling 102, via the temperature controller 16, the temperature of the one or more components 20, 22, and 24 to stay at or near a set-temperature that is based at least in part on a desired margin of safety and the acid dew point. Additionally, controlling 100 the temperature of the one or more components 20, 22, and 24 such that the temperature of the one or more components 20, 22, and 24 is above an acid dew point of the flue gas 12 may include controlling 104, via the temperature controller 16, the temperature of the working-medium 26 contained within the conduit 32 formed by the one or more components 20, 22, and 24. In embodiments, the flue gas analyzer 18, the temperature controller 16, and the heating device 48 may form a closed control loop.

Figure 6:
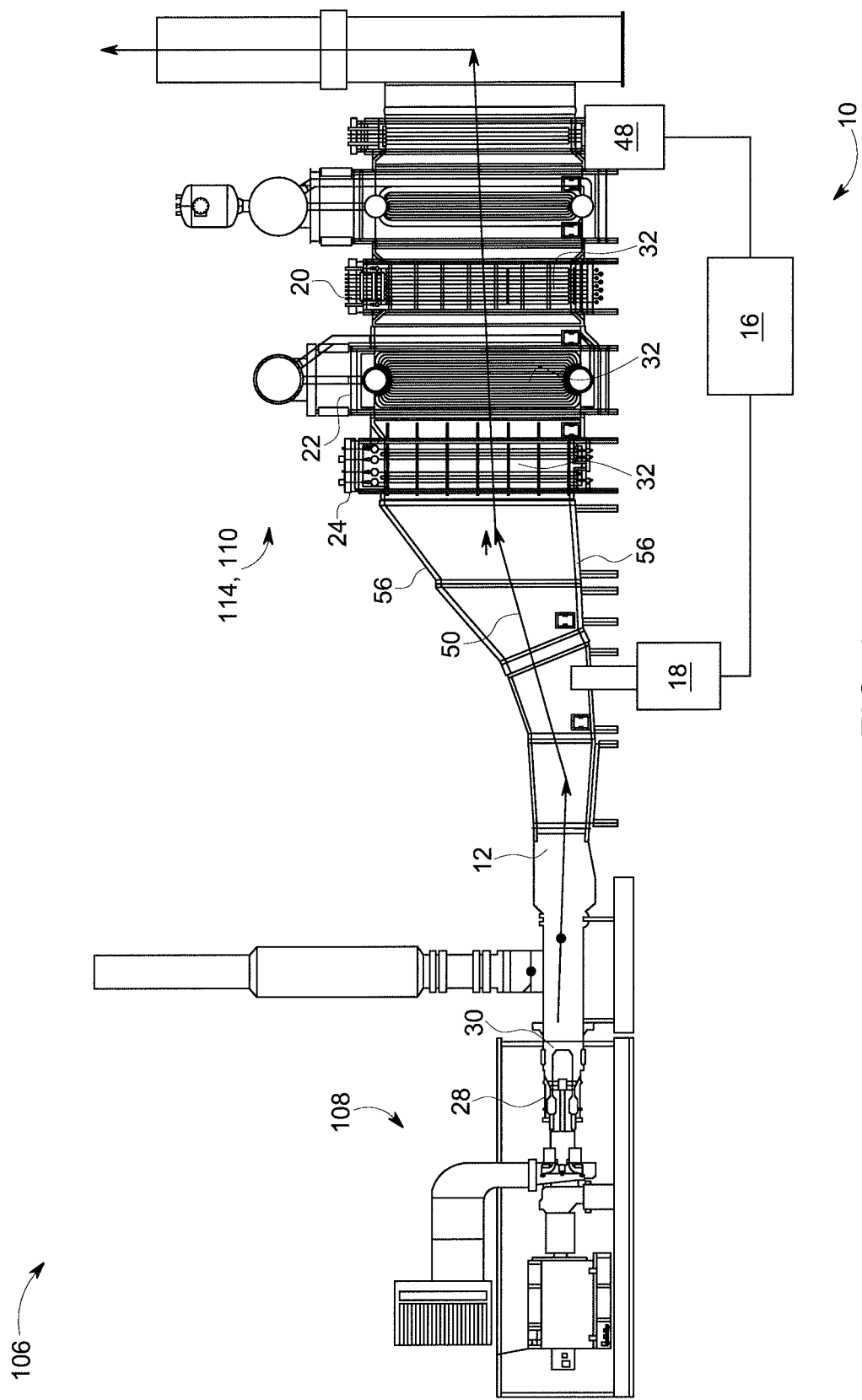
FIG. 6 is another diagram of the system of FIG. 1, wherein the steam generator is an HRSG in a combined cycle power generation plant.

Referring now to FIG. 6, the system 10 may be implemented in a combined cycle power generation plant ("CCPGP") 106. The CCPGP 106 may include a primary generator 108, a secondary generator 110, the temperature controller 16, and the flue gas analyzer 18. The primary generator 108 may generate the flue gas 12 by combusting a fuel 28 in a combustion chamber 30. For example, in embodiments, the primary generator 108 may be a gas-fired turbine as shown in FIG. 6. It is to be appreciated, however, that in embodiments, the primary generator 108 may be a steam turbine powered by a boiler (14 in FIG. 1). In such embodiments, the boiler may be an oil-fired boiler, a gas-fired boiler, or a coal-fired boiler.

As shown in FIG. 6, the secondary generator 110 may be a steam turbine (not shown) powered by a steam generator 114 which may be an HRSG. In such embodiments, the HRSG 114 may be fluidly connected to the primary generator 108 such that the flue gas 12 flows from the combustion chamber 30 of the primary generator 108 to the HRSG 114. In embodiments, the CCPGP 106 may further include the one or more components 20, 22, and 24, which may be disposed in at least one of the primary generator 108 and the secondary generator 110. For example, in embodiments where the primary generator 108 is powered by a boiler (14 in FIG. 1), the one or more components 20, 22, and 24 may be disposed in the boiler as discussed above and as shown in FIG. 1. Additionally, in embodiments where the secondary generator 110 is powered by an HRSG 114, the secondary generator 110 may include the one or more components 20, 22, and 24 which form the conduit 32 as shown in FIG. 6. As stated above, the one or more components may include an economizer 20, evaporator 22, and/or superheater 24.

As is to be appreciated, in embodiments, in which the system 10 is applied to an HRSG 114, the temperature controller 16 and the flue gas analyzer 18 function in a manner similar to those discussed and shown above in connection with the boiler (14 in FIG. 1). As is also to be appreciated, in embodiments where the primary generator 108 is powered by a boiler (14 in FIG. 1) and the secondary generator 110 is powered by the HRSG 114, the system 10 may be expanded such that the temperature controller 16 controls the temperature of the one or more components 20, 22, and 24, of both the boiler (14 in FIG. 1) and the HRSG (114 in FIG. 6).

It is to be further understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system 10 may include at least one processor 44, and system memory 46, which may include random access memory (RAM) and read-only memory (ROM). The system 10 may further include an input/output controller, and one or more data storage structures. All of these latter elements may be in communication with the at least one processor 44 to facilitate the operation of the system 10 as discussed above. Suitable computer program code may be provided for executing numerous functions, including those discussed above in connection with the system 10 and method 96 disclosed herein. The computer program code may also include program elements such as an operating system, a database management system and "device drivers" that allow the system 10, to interface with computer peripheral devices, e.g., sensors, a video display, a keyboard, a computer mouse, etc.

The at least one processor 44 of the system 10 may include one or more conventional microprocessors and one or more supplementary co-processors such as math co-processors or the like. Elements in communication with each other need not be continually signaling or transmitting to each other. On the contrary, such elements may transmit to each other as necessary, may refrain from exchanging data at certain times, and may cause several steps to be performed to establish a communication link therebetween.

The data storage structures such as memory discussed herein may include an appropriate combination of magnetic, optical and/or semiconductor memory, and may include, for example, RAM, ROM, flash drive, an optical disc such as a compact disc and/or a hard disk or drive. The data storage structures may store, for example, information required by the system 10 and/or one or more programs, e.g., computer program code such as the application stored in memory device 46 and/or other computer program product, adapted to direct the system 10. The programs may be stored, for example, in a compressed, an uncompiled and/or an encrypted format, and may include computer program code. The instructions of the computer program code may be read into a main memory of a processor from a computer-readable medium. While execution of sequences of instructions in the program causes the processor to perform the process steps described herein, hard-wired circuitry may be used in place of, or in combination with, software instructions for implementation of the processes of the present invention. Thus, embodiments of the present invention are not limited to any specific combination of hardware and software.

The program may also be implemented in programmable hardware devices such as field programmable gate arrays, programmable array logic, programmable logic devices or the like. Programs may also be implemented in software for execution by various types of computer processors. A program of executable code may, for instance, include one or more physical or logical blocks of computer instructions, which may, for instance, be organized as an object, procedure, process or function. Nevertheless, the executables of an identified program need not be physically located together, but may include separate instructions stored in different locations which, when joined logically together, form the program and achieve the stated purpose for the programs such as preserving privacy by executing the plurality of random operations. In an embodiment, an application of executable code may be a compilation of many instructions, and may even be distributed over several different code partitions or segments, among different programs, and across several devices.

The term "computer-readable medium" as used herein refers to any medium that provides or participates in providing instructions to at least one processor 44 of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to at least one processor for execution. For example, the instructions may initially be borne on a magnetic disk of a remote computer (not shown). The remote computer can load the instructions into its dynamic memory and send the instructions over an Ethernet connection, cable line, or telephone line using a modem. A communications device local to a computing device, e.g., a server, can receive the data on the respective communications line and place the data on a system bus for at least one processor. The system bus carries the data to main memory, from which the at least one processor retrieves and executes the instructions. The instructions received by main memory may optionally be stored in memory either before or after execution by the at least one processor. In addition, instructions may be received via a communication port as electrical, electromagnetic or optical signals, which are exemplary forms of wireless communications or data streams that carry various types of information.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for regulating condensation of a flue gas in a steam generator is provided. The system includes a temperature controller and a flue gas analyzer. The temperature controller is configured to control a temperature of a component of the steam generator, the component being in heating-contact with the flue gas. The flue gas analyzer is configured to communicate with the temperature controller and to obtain a measurement of an amount of an acid-forming compound in the flue gas. The temperature controller adjusts the temperature of the component based at least in part on the measurement such that the temperature of the component is above an acid dew point of the flue gas when the component is in heating-contact with the flue gas. In certain embodiments, the temperature controller is further configured to keep the temperature of the component at or near a set temperature that is based at least in part on a desired margin of safety and the acid dew point. In certain embodiments, the acid-forming compound is sulfur-trioxide. In certain embodiments, the flue gas analyzer is further configured to obtain the measurement of the amount of the acid-forming compound when the flue gas has a temperature between 400° C. and 800° C. In certain embodiments, the flue gas analyzer obtains the measurement of the acid-forming compound via a Raman process. In certain embodiments, the Raman process is a stimulated Raman process and the flue gas analyzer includes two or more laser diodes. In certain embodiments, the flue gas analyzer obtains the measurement of the acid-forming compound via IR absorption. In certain embodiments, the steam generator is at least one of a heat recovery steam generator, a gas-fired boiler, an oil-fired boiler, and a coal-fired boiler. In certain embodiments, the component forms a conduit that contains a working-medium, and the temperature controller controls the temperature of the component via controlling a temperature of the working-medium.

Other embodiments provide for a method for regulating condensation of a flue gas in a steam generator. The method includes obtaining a measurement of an amount of an acid-forming compound in the flue gas via a flue gas analyzer, the flue gas being in heating-contact with one or more components of the steam generator. The method further includes controlling a temperature of the one or more components via a temperature controller in communication with the flue gas analyzer and based at least in part on the measurement such that the temperature of the one or more components is above an acid dew point of the flue gas. In certain embodiments, controlling a temperature of the one or more components via a temperature controller in communication with the flue gas analyzer and based at least in part on the measurement such that the temperature of the one or more components is above an acid dew point of the flue gas includes controlling the temperature of the one or more components via the temperature controller to stay at or near a set-temperature that is based at least in part on a desired margin of safety and the acid dew point. In certain embodiments, the acid-forming compound is sulfur-trioxide. In certain embodiments, the flue gas analyzer obtains the measurement of the amount of the acid-forming compound when the flue gas has a temperature between 400° C. and 800° C. In certain embodiments, the flue gas analyzer obtains the measurement of the acid-forming compound via a Raman process. In certain embodiments, the Raman process is a stimulated Raman process and the flue gas analyzer includes two or more laser diodes. In certain embodiments, the flue gas analyzer obtains the measurement of the acid-forming compound via IR absorption. In certain embodiments, the steam generator is at least one of a heat recovery steam generator, a gas-fired boiler, an oil-fired boiler, and a coal-fired boiler. In certain embodiments, controlling a temperature of the one or more components via a temperature controller in communication with the flue gas analyzer and based at least in part on the measurement such that the temperature of the one or more components is above an acid dew point of the flue gas includes controlling a temperature of a working-medium contained within a conduit formed by the one or more components via the temperature controller.

Yet still other embodiments provide for a combined cycle power generation plant that regulates condensation of a flue gas. The combined cycle power generation plant includes a primary generator, a heat recovery steam generator, one or more components, a temperature controller, and a flue gas analyzer. The primary generator generates the flue gas by combusting a fuel. The heat recovery steam generator is fluidly connected to the primary generator such that the flue gas flows from the primary generator to the heat recovery steam generator. The one or more components are disposed in at least one of the primary generator and the heat recovery steam generator, and are configured to be in heating-contact with the flue gas. The temperature controller is configured to control a temperature of the one or more components. The flue gas analyzer is in communication with the temperature controller and is configured to obtain a measurement of an acid-forming compound in the flue gas. The temperature controller adjusts the temperature of the one or more components based at least in part on the measurement such that the temperature of the one or more components is above an acid dew point of the flue gas when the one or more components are in heating-contact with the flue gas. In certain embodiments, the flue gas analyzer is further configured to obtain, via a stimulated Raman process, the measurement of the amount of the acid-forming compound at a location within the combined cycle power generation plant where the flue gas has a temperature between 400° C. and 800° C., and the acid-forming compound is sulfurtrioxide. In certain embodiments, the flue gas analyzer is further configured to obtain, via IR absorption, the measurement of the amount of the acid-forming compound at a location within the combined cycle power generation plant where the flue gas has a temperature between 400° C. and 800° C. In certain embodiments, the fuel combusted by the primary generator is at least one of a gas, an oil, and a coal.

Accordingly, as is to be appreciated, by measuring the amount of the acid-forming compounds in a flue gas, some embodiments of the present invention provide for the temperature of the working-medium to be at a lower temperature when it enters the steam generator without increasing the risk of corrosion to the components of the steam generator, i.e. boiler or HRSG. In turn, allowing the temperature of the working-medium to be lower when it enters the steam generator increases the approach-point, which in turn increases the steam generator's efficiency. For example, by increasing the approach point, some embodiments provide for reduction of the "pinch point" of the steam generator. As used herein, the term "pitch point" refers to the difference in the temperature of the flue gas as it leaves the steam generator and the temperature of the generated steam that leaves the steam generator. By reducing the pitch point, some embodiments may increase the efficiency of a steam generator by several tenths of a percentage (0.1%).

Moreover, in some embodiments, the flue gas analyzer and the temperature controller provide for real time or near real time measurements of the amount of the acid-forming compounds in the flue gas, which in turn further provides for the real time or near real time adjustment of the approach point while maintaining the desired margin of safety. By providing for real time or near real time adjustment of the approach point, some embodiments may allow for the margin of safety to be lowered without increasing the risk of corrosion due to condensation of acid-forming compounds than would otherwise be possible. Additionally, such embodiments may also reduce the risk of corrosion to the components of a steam generator which are exposed to a flue gas. For example, real time or near real time measurements of the amount of the acid-forming compounds in the flue gas allow some embodiments to adjust the temperature of one or more components as the acid dew point fluctuates. Thus, in such embodiments, the chance that the temperature of the components in heating-contact with the flue gas will be at or below the acid due point is reduced.

Further, by measuring the amount of SO3 in a flue gas at a temperature between 400° C. and 800° C., some embodiments resolve ambiguities regarding conversion of SOx compounds/chemistry as the flue gas cools. In other words, by measuring the amount of SO3 in the flue gas between 400° C. and 800° C., some embodiments provide for an accurate measurement of the total amount of the acid-forming compounds in the flue gas, which in turn provides for an accurate calculation of the acid dew point.

As is to be appreciated, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for regulating condensation of a flue gas in a steam generator, the system comprising:
   a temperature controller configured to control a temperature of a component of the steam generator, the temperature controller comprising a heater in heating contact with a working medium of the steam generator, the component being in heating-contact with the flue gas;
   a flue gas analyzer configured to communicate with the temperature controller and to obtain a measurement of an amount of an acid-forming compound in the flue gas, wherein the flue gas analyzer is further configured to obtain the measurement of the amount of the acid-forming compound at a predetermined location where the flue gas has a temperature between 400° C. and 800° C.; and wherein the temperature controller adjusts the temperature of the component based at least in part on the measurement such that the temperature of the component is above an acid dew point of the flue gas when the component is in heating-contact with the flue gas.

2. The system of claim 1, wherein the temperature controller is further configured to keep the temperature of the component at or near a set temperature that is based at least in part on a desired margin of safety and the acid dew point.

3. The system of claim 1, wherein the acid-forming compound is sulfur-trioxide.

4. The system of claim 1, wherein the flue gas analyzer is further configured to obtain the measurement of the amount of the acid-forming compound when the flue gas has a temperature of 500° C.

5. The system of claim 1, wherein the flue gas analyzer obtains the measurement of the acid-forming compound via a Raman process.

6. The system of claim 5, wherein the Raman process is a stimulated Raman process and the flue gas analyzer comprises two or more laser diodes.

7. The system of claim 1, wherein the flue gas analyzer obtains the measurement of the acid-forming compound via IR absorption.

8. The system of claim 1, wherein the component forms a conduit that contains a working-medium, and the temperature controller controls the temperature of the component via controlling a temperature of the working-medium.

9. A method for regulating condensation of a flue gas in a steam generator, the method comprising:

obtaining a measurement of an amount of an acid-forming compound in the flue gas at a predetermined location via a flue gas analyzer, the flue gas being in heating-contact with one or more components of the steam generator, wherein the measurement of the amount of the acid-forming compound is obtained by the flue gas analyzer at the predetermined location where the flue gas has a temperature between 400° C. and 800° C.; and controlling a temperature of the one or more components via a temperature controller in communication with the flue gas analyzer, the temperature controller comprising a heater in heating contact with a working medium of the steam generator;

wherein, at least in part based on the measurement of the amount of the acid-forming compound in the flue gas, the temperature of the one or more components is maintained above an acid dew point of the flue gas.

10. The method of claim 9, wherein controlling a temperature of the one or more components via a temperature controller in communication with the flue gas analyzer and based at least in part on the measurement such that the temperature of the one or more components is above an acid dew point of the flue gas comprises:

controlling the temperature of the one or more components via the temperature controller to stay at or near a set-temperature that is based at least in part on a desired margin of safety and the acid dew point.

11. The method of claim 9, wherein the acid-forming compound is sulfur-trioxide.

12. The method of claim 9, wherein the flue gas analyzer obtains the measurement of the amount of the acid-forming compound when the flue gas has a temperature of 500° C.

13. The method of claim 9, wherein the flue gas analyzer obtains the measurement of the acid-forming compound via a Raman process.

14. The method of claim 13, wherein the Raman process is a stimulated Raman process and the flue gas analyzer comprises two or more laser diodes.

15. The method of claim 9, wherein the flue gas analyzer obtains the measurement of the acid-forming compound via IR absorption.

16. The method of claim 9, wherein the steam generator is at least one of a heat recovery steam generator, a gas-fired boiler, an oil-fired boiler, and a coal-fired boiler.

17. The method of claim 9, wherein controlling a temperature of the one or more components via a temperature controller in communication with the flue gas analyzer and based at least in part on the measurement such that the temperature of the one or more components is above an acid dew point of the flue gas comprises:

controlling a temperature of a working-medium contained within a conduit formed by the one or more components via the temperature controller.

18. A combined cycle power generation plant that regulates condensation of a flue gas, the combined cycle power generation plant comprising:

a primary generator that generates the flue gas by combusting a fuel;

a heat recovery steam generator fluidly connected to the primary generator such that the flue gas flows from the primary generator to the heat recovery steam generator;

one or more components disposed in at least one of the primary generator and the heat recovery steam generator, the one or more components configured to be in heating-contact with the flue gas;

a temperature controller configured to control a temperature of the one or more components, the temperature controller comprising a heater in heating contact with a working medium of the heat recovery steam generator;

a flue gas analyzer in communication with the temperature controller and configured to obtain a measurement of an acid-forming compound in the flue gas at a predetermined location where the temperature of the flue gas is between 400° C. and 800° C.; and wherein the temperature controller adjusts the temperature of the one or more components based at least in part on the measurement such that the temperature of the one or more components is above an acid dew point of the flue gas when the one or more components are in heating-contact with the flue gas.

19. The combined cycle power generation plant of claim 18, wherein the flue gas analyzer is further configured to obtain, via a stimulated Raman process, the measurement of the amount of the acid-forming compound at the predetermined location, and the acid-forming compound is sulfur-trioxide.

20. The combined cycle power generation plant of claim 18, wherein the flue gas analyzer is further configured to obtain, via IR absorption, the measurement of the amount of the acid-forming compound at the predetermined location.

* * * * *